United States Patent [19]

Bosies et al.

[11] Patent Number: 5,206,253
[45] Date of Patent: Apr. 27, 1993

[54] DISPHOSPHONIC ACID DERIVATIVES, PROCESSES FOR THEIR PRODUCTION AND PHARMACEUTICAL PREPARATIONS CONTAINING THESE COMPOUNDS

[75] Inventors: Elmar Bosies, Weinheim; Frieder Bauss, Lambsheim, both of Fed. Rep. of Germany

[73] Assignee: Boehringer Mannheim, GmbH, Mannheim, Fed. Rep. of Germany

[21] Appl. No.: 776,407

[22] PCT Filed: May 18, 1990

[86] PCT No.: PCT/EP90/00798
§ 371 Date: Nov. 25, 1991
§ 102(e) Date: Nov. 25, 1991

[87] PCT Pub. No.: WO90/14348
PCT Pub. Date: Nov. 29, 1990

[30] Foreign Application Priority Data
May 26, 1989 [DE] Fed. Rep. of Germany ....... 3917153

[51] Int. Cl.⁵ .............. A61K 31/41; A61K 31/42; A61K 31/415; C07F 9/06
[52] U.S. Cl. ................... 514/363; 514/364; 514/365; 514/370; 514/372; 514/374; 514/377; 514/378; 514/380; 514/383; 514/381; 514/398; 514/399; 548/112
[58] Field of Search .............. 548/112; 514/398, 399, 514/365, 370, 372, 374, 377, 378, 380, 383, 363, 364, 381

[56] References Cited
PUBLICATIONS
CA 99(25)212705c Antiinflammatory and antiarthritic pyrazolylethane phosphonates, Biere et al., p. 662, 1983.
CA 114(25)164505s Preparation of . . . regulators, Bosies et al. p. 806, 1991.

*Primary Examiner*—Mary C. Lee
*Assistant Examiner*—Joseph K. McKane
*Attorney, Agent, or Firm*—Nikaido, Marmelstein, Murray & Oram

[57] ABSTRACT

The present invention concerns novel disphosphonates having the general formula I

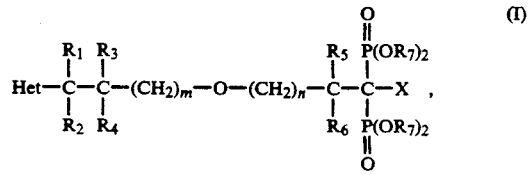

in which
Het represents a heterocyclic five-membered ring with 2-4 heteroatoms which is substituted, if desired, and which can also be partially hydrogenated,
$R_1$–$R_7$ each denote, independently of each other, hydrogen or $C_1$–$C_5$ alkyl,
X=denotes hydrogen, OH or the group —$NR_8R_9$, in which $R_8$ and $R_9$ should each be, independently of each other, hydrogen or $C_1$–$C_5$ alkyl,
m and n denote, independently of each other, 0, 1 or 2,
as well as their pharmacologically safe salts and optically active forms.

6 Claims, No Drawings

DISPHOSPHONIC ACID DERIVATIVES, PROCESSES FOR THEIR PRODUCTION AND PHARMACEUTICAL PREPARATIONS CONTAINING THESE COMPOUNDS

The present invention concerns novel diphosphonic acid derivatives, processes for their production as well as pharmaceutical preparations which contain these substances.

Diphosphonic acid derivatives are described in DE-PS 18 13 659 of which 1-hydroxyethane-1,1-diphosphonic acid has gained importance as an agent for the treatment of Paget's disease.

1,1-diphosphonates are described in EP 274 158 whose alkyl chain is substituted by a piperidine ring and interrupted by a heteroatom.

In addition 1,1-diphosphonic acids are described in EP 186 405 whose alkyl chain is substituted by 6-membered heterocyclic rings and interrupted by a heteroatom.

It was found that alkane-1,1-diphosphonic acids substituted by 5-membered heterocyclic rings in which the alkyl chain is interrupted by oxygen show a substantially more pronounced effect on calcium metabolism than the previously known compounds. These substances are therefore particularly suitable for treating a wide range of disturbances in calcium metabolism. In particular they can be applied particularly effectively in cases where the build-up and break-down of bone is disturbed, i.e. they are suitable for the treatment of diseases of the skeletal system such as e.g. osteoporosis, Paget's disease, Bechterew's disease among others. On the basis of these properties they can, however, also be used in the treatment of bone metastases, urolithiasis and for the prevention of heterotopic ossifications. Since they influence calcium metabolism they in addition form a basis for the treatment of rheumatoid arthritis, osteoarthritis and degenerative arthrosis.

The present invention thus provides diphosphonates having the general formula I

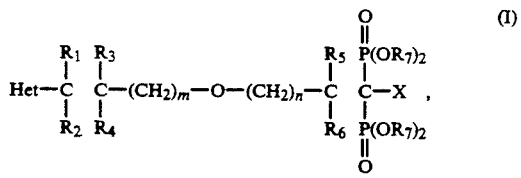

in which
Het is selected from the group consisting of a pyrazolyl, imidazolyl, thiazolyl, isothiazolyl, oxazolyl, isoxazolyl, triazolyl, thiadiazolyl, oxadiazolyl, dithiazolyl and tetrazolyl ring as well as their dihydro and tetrahydro derivatives, which ring can be partially hydrogenated and is unsubstituted or substituted at least once by $C_1$-$C_6$ alkyl, halogen, amino or $CF_3$,
$R_1$-$R_7$ each denote, independently of each other, hydrogen or $C_1$-$C_5$ alkyl,
$X$=denotes hydrogen, OH or the group —$NR_8R_9$, in which $R_8$ and $R_9$ should each be, independently of each other, hydrogen or $C_1$-$C_5$ alkyl,
m and n denote, independently of each other, 0, 1 or 2,
as well as their pharmacologically safe salts.

In this connection Het is understood as a ring such as the pyrazole, imidazole, thiazole, isothiazole, oxazole, isoxazole, 1,2,3-thiazole, 1,2,4-triazole, 1,2,3-thiadiazole, 1,3,4-thiadiazole, 1,2,4-thiadiazole, 1,2,5-thiadiazole, 1,2,3-oxadiazole, 1,3,4-oxadiazole, 1,2,4-oxadiazole, 1,2,5-oxadiazole, 1,2,3-dithiazole, 1,3,4-dithiazole, 1,2,4-dithiazole and tetrazole ring as well as their hydrogenated or partially hydrogenated derivatives such as for example dihydro and tetrahydro derivatives.

In this connection the pyrazole, imidazole, thiazole and 1,2,5-thiadiazole ring and in particular the imidazole and 4,5-dihydroimidazole ring are preferred.

The heterocylic rings can, if desired, be substituted once or twice by $C_1$-$C_6$ alkyl groups, preferably a methyl, ethyl or isopropyl group, as well as by halogen, the amino or $CF_3$ group.

Halogen is understood as fluorine, chlorine or bromine.

$C_1$-$C_5$ alkyl should preferably represent a methyl, ethyl or isopropyl group. The group —$NR_8R_9$ is preferably an amino, dimethylamino or diethylamino group.

X preferably represents hydrogen or hydroxy, the value of n is preferably 0.

Asymmetric carbon atoms can be in the R or S configuration and the compounds can be present in an optically active form or as a racemic mixture. They are also provided by the present invention. The enantiomeric derivatives can be obtained by using optically pure precursors.

Compounds having the general formula I are prepared by well-known methods, preferably by
I. in case X in the general formula I denotes OH,
a) a carboxylic acid having the general formula II

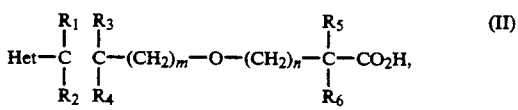

in which Het, $R_1$-$R_6$, m and n have the meanings set forth above, is reacted with a mixture of phosphorous acid or phosphoric acid and a phosphorus halide or phosphoroxyhalide and subsequently saponified to form the free diphosphonic acid, or b) a carboxylic acid chloride having the general formula III

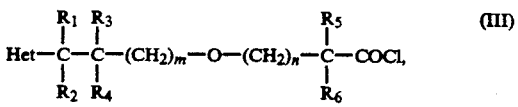

in which Het, $R_1$-$R_6$, m and n have the aforementioned meanings, is reacted with a trialkyl phosphite having the general formula IV

in which R' represents alkyl residues with 1-4 carbon atoms, preferably methyl, ethyl, isopropyl and isobutyl, to form an acylphosphonate having the general formula V $$\text{Het}-\underset{\underset{R_2}{|}}{\overset{\overset{R_1}{|}}{C}}-\underset{\underset{R_4}{|}}{\overset{\overset{R_3}{|}}{C}}-(CH_2)_m-O-(CH_2)_n-\underset{\underset{R_6}{|}}{\overset{\overset{R_5}{|}}{C}}-\overset{\overset{O}{\|}}{C}-\overset{\overset{O}{\|}}{P}(OR')_2, \quad (V)$$

in which Het, $R_1$-$R_6$, m, n and R' have the aforementioned meanings, which is subsequently allowed to react with a dialkylphosphite having the general formula VI $$H-\overset{\overset{O}{\|}}{P}(OR')_2, \quad (VI)$$

in which R' has the meaning stated above, to form a diphosphonate having the general formula VII $$\text{Het}-\underset{\underset{R_2}{|}}{\overset{\overset{R_1}{|}}{C}}-\underset{\underset{R_4}{|}}{\overset{\overset{R_3}{|}}{C}}-(CH_2)_m-O-(CH_2)_n-\underset{\underset{R_6}{|}}{\overset{\overset{R_5}{|}}{C}}-\underset{\underset{\overset{\|}{O}}{P(OR')_2}}{\overset{\overset{P(OR')_2}{\overset{\|}{O}}}{C}}-OH, \quad (VII)$$

in which Het, $R_1$-$R_6$, m, n and R' have the meanings stated above, and, if desired, the tetraesters which formed are saponified to diesters or acids having the general formula I, or c) in case n=0, a compound having the general formula VIII $$\text{Het}-\underset{\underset{R_2}{|}}{\overset{\overset{R_1}{|}}{C}}-\underset{\underset{R_4}{|}}{\overset{\overset{R_3}{|}}{C}}-(CH_2)_m-O-H, \quad (VIII)$$

in which Het, $R_1$-$R_4$ and m have the meanings set forth above, is allowed to react with an epoxide having the general formula IX $$\underset{R_6}{\overset{R_5}{\diagdown}}\underset{\diagdown}{\overset{O}{\diagup}}\underset{\underset{\overset{\|}{O}}{P(OR')_2}}{\overset{P(OR')_2}{\diagup}}, \quad (IX)$$

in which $R_5$, $R_6$ and R' have the meanings set forth above and the diphosphonic acid derivative which formed having the general formula X $$\text{Het}-\underset{\underset{R_2}{|}}{\overset{\overset{R_1}{|}}{C}}-\underset{\underset{R_4}{|}}{\overset{\overset{R_3}{|}}{C}}-(CH_2)_m-O-\underset{\underset{R_6}{|}}{\overset{\overset{R_5}{|}}{C}}-\underset{\underset{\overset{\|}{O}}{P(OR')_2}}{\overset{\overset{P(OR')_2}{}}{C}}-OH, \quad (X)$$

is saponified, if desired, to diesters or acids, or

II. in case X in the general formula I denotes the group $-NR_8R_9$, a carboxylic acid derivative having the general formula XI $$\text{Het}-\underset{\underset{R_2}{|}}{\overset{\overset{R_1}{|}}{C}}-\underset{\underset{R_4}{|}}{\overset{\overset{R_3}{|}}{C}}-(CH_2)_m-O-(CH_2)_n-\underset{\underset{R_6}{|}}{\overset{\overset{R_5}{|}}{C}}-A, \quad (XI)$$

in which Het, $R_1$-$R_6$, m, and n have the meanings stated above, and A represents a nitrile, iminoether or a $-CONR_8R_9$ group, in which $R_8$ and $R_9$ have the meanings set forth above, is reacted with a phosphorus compound having the general formula XII $$PT_3 \quad (XII),$$

in which T denotes halogen, OH or OR', whereby R' has the meaning stated above, and subsequently saponified, if desired, or III. in case X in the general formula I denotes hydrogen, a) a compound having the general formula XIII $$\text{Het}-\underset{\underset{R_2}{|}}{\overset{\overset{R_1}{|}}{C}}-\underset{\underset{R_4}{|}}{\overset{\overset{R_3}{|}}{C}}-(CH_2)_m-U, \quad (XIII)$$

in which Het, $R_1$-$R_4$ and m have the meanings set forth above and U represents a reactive group such as e.g. halogen or a sulfonate, is reacted with a diphosphonic acid derivative having the general formula XIV, $$HO-(CH_2)_n-\underset{\underset{R_6}{|}}{\overset{\overset{R_5}{|}}{C}}-\underset{\underset{\overset{\|}{O}}{P(OR')_2}}{\overset{\overset{P(OR')_2}{\overset{\|}{O}}}{C}}-H, \quad (XIV)$$

in which $R_5$, $R_6$, R' and n have the meanings set forth above and, if desired, the tetraesters which formed are saponified to diesters or acids, or b) a compound having the general formula VIII $$\text{Het}-\underset{\underset{R_2}{|}}{\overset{\overset{R_1}{|}}{C}}-\underset{\underset{R_4}{|}}{\overset{\overset{R_3}{|}}{C}}-(CH_2)_m-O-H, \quad (VIII)$$

in which Het, $R_1$-$R_4$ and m have the meanings stated above, is added to a compound having the general formula XV $$\underset{R_6}{\overset{R_5}{\diagdown}}C=C\underset{\underset{\overset{\|}{O}}{P(OR')_2}}{\overset{P(OR')_2}{\diagup}}, \quad (XV)$$

in which $R_5$, $R_6$ and R' have the meanings stated above, and if desired, the tetraesters which form are saponified to diesters or acids, or c) a compound having the general formula XVI

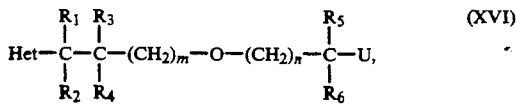

in which Het $R_1$-$R_6$, U, m and n have the meanings set forth above, is reacted with a diphosphonic acid derivative having the general formula XVII

in which R' has the meaning set forth above, and if desired, the tetraesters which formed are saponified to diesters or acids, or in case $R_6$ denotes hydrogen d) a compound having the general formula XVIII

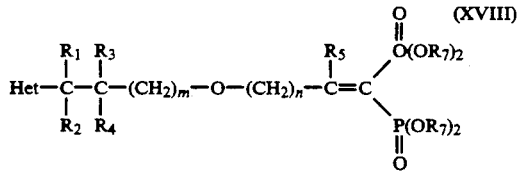

in which Het, $R_1$-$R_5$ and $R_7$, m and n have the meanings set forth above is hydrogenated catalytically
and, if desired, the tetraesters which formed are subsequently saponified to diesters or acids and, if desired, are converted into pharmacologically safe salts.

The carboxylic acids of the general formula II used in process I a) are reacted with 1-2, preferably 1.5 mol phosphorous acid or phosphoric acid and 1-2, preferably 1.5 mol phosphorus trihalide or phosphoroxyhalide at temperatures of 80°-130° C., preferably 100°-110° C. The reaction can also be carried out in the presence of diluting agents such as halogen-hydrocarbons, in particular chlorobenzene, tetrachloroethane or also sulfolan or dioxan. The subsequent hydrolysis is carried out by boiling with water, it is, however, expedient to use half-concentrated hydrochloric or hydrobromic acid. In the said process phosphorus trichloride or phosphorus tribromide may for example be used as phosphorus trihalides and phosphoroxychloride is preferred above all as the phosphoroxyhalide.

In process I b) the acid chloride having the general formula III is allowed to react with the trialkyl phosphite having the general formula IV at temperatures between 0° and 60° C., preferably 20°-40° C. It can be carried out without solvents or also in the presence of inert solvents such as diethyl ether, tetrahydrofuran, dioxan or even halogenated hydrocarbons such as e.g. methylene chloride. The acyl phosphonate having the general formula V which forms as an intermediate can be isolated or immediately reacted further. The subsequent reaction is carried out in the presence of a weak base, preferably a secondary amine such as e.g. dibutyl amine at a temperature of 0°-60° C., preferably at 10°-30° C. The acid hydrolysis can be carried out very well by boiling with half-concentrated hydrochloric acid or hydrobromic acid.

In process I c), the alcohols having the general formula VIII are usually used in the form of their alkali salts, preferably as sodium salts. Toluene, dioxan, tetrahydrofuran or even dimethyl formamide is preferably used as the solvent; the reactions are carried out between 20° and 80° C.

In process II the nitriles having the general formula XI are reacted with phosphorous acid at temperatures of 110°-180° C. The reaction can be carried out without or in the presence of aprotic solvents such as e.g. diethylene glycol dimethylether or diethylene glycol dimethyl ether. One can, however, also react the nitriles with a phosphorus trihalide, e.g. phosphorus tribromide or phosphorus trichloride, in an inert solvent such as e.g. dioxan or tetrahydrofuran, if desired with addition of water, at temperatures of 20°-80° C. Iminoethers having the general formula XI are allowed to react with dialkyl phosphites, preferably in the presence of equimolar amounts of sodium, in inert solvents such as diethyl ether, dioxan or even benzene, whereby the reactions usually take place at the reflux temperature of the corresponding solvent. Acid amides having the general formula XI can be reacted in inert solvents such as e.g. halogenated hydrocarbons or ethers such as e.g. diethyl ether, with a mixture of phosphorus pentahalide/phosphorous acid or even oxalylchloride/trialkylphosphite.

In process III a) the diphosphonic acid derivative having the general formula XIV is used in the form of a sodium or potassium salt. For this it is reacted with sodium, potassium or the corresponding hydride in an inert solvent such as e.g. benzene, toluene or dimethyl formamide at a temperature of 0° to 40° C., preferably at 25° C. The alkali salt is reacted with the corresponding halide or sulfonate without being isolated. The temperature for this is 20°-110° C.

In process III b) the alcohols having the general formula VIII are used in the form of their alkali salts, preferably the sodium salts. For this purpose they are reacted with sodium or sodium hydride in an inert solvent such as benzene, toluene, dioxan or dimethyl formamide at a temperature of 0°-60° C., preferably at 25° C. The alkali salt is usually reacted, without isolation, with the corresponding diphosphonate having the general formula XV. The temperature is 20°-80° C.

In process III c) the methane diphosphonic acid ester having the general formula XVII is used in the form of its sodium or potassium salt. For this purpose it is reacted with sodium, potassium or the corresponding hydride in an inert solvent such as e.g. benzene, toluene or dimethyl formamide at a temperature of 0° to 40° C., preferably at 25° C. The alkali salt is reacted without isolation, with the corresponding halide or sulfonate. The temperature in this case is 20°-110° C.

The hydrogenation in process III d is carried out in the presence of a nobel metal catalyst such as e.g. palladium on carbon or platinum in an alcohol such as methanol or ethanol as solvent or also in water. One can, however, also use nickel in an alkaline medium.

Optically active compounds having the formula I are usually produced by using optically active parent compounds.

The carboxylic acids having the formula II which are used in process I a are usually produced in the following manner.

The corresponding Het-alkanol having the formula VIII is reacted with a haloalkanoic acid ester, preferably when n=0, with a haloacetic acid ester such as e.g. ethyl bromoacetate or ethyl chloroacetate. The carboxylic acid ester which is formed is subjected to an acidic or alkaline saponification using the usual methods.

The Het-alkanols having the formula VIII used in this process as well as in process I c and III b are as a rule known from the literature or they can be easily produced from the corresponding amino acids or their esters by reduction with e.g. lithium aluminium hydride (c.f. e.g. Bull.Soc.Chim. France 1969, 2835).

Carboxylic acid chlorides having the general formula III can be produced by conventional methods from the carboxylic acids having the general formula II described above e.g. by reaction with thionyl chloride or phosphorus pentachloride.

Some of the epoxides used in process I c having the general formula IX are known from the literature (c.f. e.g. U.S. Pat. No.3,940,436) or can be produced according to the cited methods.

The nitriles or amides used in process II having the formula XI can be synthesized from the corresponding Het-alkanols of formula VIII by reaction with haloalkanoic acid nitriles or haloalkanoic acid amides. The corresponding iminoethers can be obtained from the nitriles obtained in this way by conventional methods e.g. by reaction with a lower alcohol in the presence of gaseous hydrogen chloride.

The compounds having the general formula XIII used in process III a are obtained by reacting a Het-alkanol of formula VIII with a phosphorus halide such as e.g. phosphorus trichloride or phosphorus tribromide or with an aliphatic or aromatic sulfochloride such as e.g. methane sulfochloride or benzene sulfochloride.

The compounds having the general formula XVIII used in process III d can e.g. be produced by elimination of a H-Y group whereby Y for example represents a halogen, preferably bromine or chlorine, or an acyloxy group such as e.g. an acetoxy, or a benzoyloxy which may be substituted or a trifluoroacetoxy group. The starting materials used for the compounds having the general formula XVIII, such as e.g. the corresponding acyloxy compounds, can be produced from the diphosphonates having the general formula I where X=OH by reaction with an acyl anhydride such as e.g. acetic anhydride or trifluoroacetic anhydride. The reaction is usually carried out by boiling in the corresponding acylating agent. The elimination of the H-Y group can be carried out by using bases such as e.g. tert. amines, in particular triethylamine, pyridine or diazabicycloundecene, in solvents such as alcohols, ethers (e.g. dioxan or tetrahydrofuran). For the cleavage of acetic acid, trifluoroacetic acid or benzoic acid which may be substituted, it is preferable to use the tetrasodium or tetrapotassium salt of the corresponding diphosphonic acid and the cleavage is carried out by heating to 180°-300° C., preferably to 180°-240° C. In this process high-boiling amines such e.g. ethylaniline or collidine are particularly suitable as heat-exchangers which at the same time bind the liberated acid as the ammonium salt. The free acids can then be released from the tetraalkali salt by for example treatment with an acidic ion exchanger (e.g. Amberlite-IR 120, H+- form).

The parent compounds set forth above can be used as racemates or as enantiomers whereby the optically active compounds are usually obtained from corresponding optically active hetero-alkane-carboxylic acids.

The tetraalkylesters which may be formed in the methods can be saponified to diesters or to the free tetraacids. The saponification to diesters is usually carried out by treating the tetraalkyl ester with an alkali halide, preferably sodium iodide in a suitable solvent such as e.g. acetone at room temperature.

In this process the symmetric diester/disodium salt is formed which can be converted, if desired, into the diester/diacid by an acidic ion exchanger. The formation of free diphosphonic acids by saponification is usually carried out by boiling with half-concentrated hydrochloric acid or hydrobromic acid. It is, however, also possible to cleave with trimethylsilylhalide, preferably the bromide or iodide. Conversely, the free diphosphonic acids can in turn be converted into the tetraalkyl esters by boiling with alkyl esters of orthoformic acid. The free diphosphonic acids having the general formula I can be isolated as free acids or in the form of their mono or dialkali salts. The alkali salts can as a rule be readily purified by reprecipitation from water/methanol or water/acetone.

Alkali or ammonium salts are especially used as salts which are pharmacologically tolerated which can be produced in the usual manner e.g. by titrating the compounds with inorganic or organic bases such as e.g. sodium or potassium hydrogen carbonate, sodium hydroxide solution, potassium hydroxide solution, aqueous ammonia or amines such as e.g. trimethylamine or triethylamine.

The novel substances according to the present invention having the formula I and their salts can be administered in a liquid or solid form either enterally or parenterally. For this purpose all the usual types of administration may be used such as tablets, capsules, coated tablets, syrups, solutions, suspensions etc. Water is preferably used as an injection medium which contains the usual additives for injection solutions such as stabilizing agents, solubilizers and buffers. Examples of such additives are tartrate and citrate buffer, ethanol, complexing agents (such as ethylenediamine tetraacetic acid and its non-toxic salts), high-molecular polymers (such as liquid polyethylene oxide) to regulate the viscosity. Liquid carriers for injection solutions must be sterile and are preferably dispensed in ampoules. Solid carriers are e.g. starch, lactose, mannitol, methylcellulose, talcum, highly-dispersed silicic acids, higher-molecular fatty acids (such as stearic acid), gelatine, agar-agar, calcium phosphate, magnesium stearate, animal and vegetable fats, solid high-molecular polymers (such as polyethylene glycols); formulations suitable for oral administration can contain flavourings and sweeteners, if desired. The dosage can depend on various factors such as the type of administration, species, age and/or individual condition. The daily doses which have to be administered are about 0.1-100 mg/person, preferably 1-20 mg/person and can be taken once or distributed over several doses.

In addition to the compounds set forth in the examples and compounds which can be derived by combining all the meanings for the substituents set forth in the claims, the following diphosphonates, as well as their sodium salts, methyl esters, ethyl esters or isopropyl esters are preferred within the scope of the present invention:

5-(imidazol-1-yl)-3-oxa-pentane-1,1-diphosphonic acid
5-(imidazol-1-yl)-3-oxa-hexane-1,1-diphosphonic acid
S-5-(imidazol-1-yl)-3-oxa-hexane-1,1-diphosphonic acid
R-5-(imidazol-1-yl)-3-oxa-hexane-1,1-diphosphonic acid
5-(imidazol-1-yl)-4-methyl-3-oxa-pentane-1,1-diphosphonic acid 5-(2-methylimidazol-1-yl)-3-oxa-hexane-1,1-diphosphonic acid
5-(4,5-dihydro-2-methylimidazol-1-yl)-3-oxa-hexane-1,1-diphosphonic acid
4-(imidazol-2-yl)-3-oxa-butane-1,1-diphosphonic acid
5-(imidazol-2-yl)-3-oxa-pentane-1,1-diphosphonic acid
5-(imidazol-2-yl)-3-oxa-hexane-1,1-diphosphonic acid
5-(imidazol-2-yl)-4-methyl-3-oxa-pentane-1,1-diphosphonic acid
4-(imidazol-4-yl)-3-oxa-butane-1,1-diphosphonic acid
5-(imidazol-4-yl)-3-oxa-pentane-1,1-diphosphonic acid
1-amino-5-(imidazol-1-yl)-3-oxa-hexane-1,1-diphosphonic acid
1-dimethylamino-5-(imidazol-1-yl)-3-oxa-hexane-1,1-diphosphonic acid The following examples show one of the variants of the process which can be used for the synthesis of the compounds according to the present invention. They are, however, not intended to limit the scope of the invention. The compounds are usually in the form of high-melting solid products (mono or disodium salt) whose structure can be ascertained by H, P and, if desired, by $^{13}C$ NMR spectroscopy. The purity of the substances was determined by means of C,H,N,P,S, Na analysis as well as by thin layer electrophoresis (cellulose, oxalate buffer of pH=4.0). In order to characterize the individual compounds the $M_{rel}$ values (=relative mobility) in relation to pyrophosphate ($M_{rel}$=1) are given.

EXAMPLE 1

1-hydroxy-5-(imidazol-1-yl)-3-oxa-oentane-1,1-diphosphonic acid 2.9 g 5-(imidazol-1-yl)-3-oxa-pentanoic acid-hydrochloride (oily substance) is fused with 2.3 g phosphorus acid at 100° C. 2.8 ml phosphorous trichloride is added dropwise and the reaction mixture is kept for 24 hours at 100° C. After cooling, 25 ml water is added, it is boiled for 1 h under reflux, filtered after cooling and the filtrate is evaporated in a vacuum. The oily residue is dissolved in 8 ml water, the solution is adjusted to a pH=5 with ca. 7 ml 10N sodium hydroxide solution and 80 ml methanol is added. After cooling with iced water a white greasy precipitate forms which is dissolved in 10 ml water and purified over 80 g ion exchanger (Amberlite IR-120, H+ form). 1.5 g=32% of the free acid which contains 1 mole water is obtained; m p.: 125°–130° C.; $M_{rel}$ 0.30.

The 5-(imidazol-1-yl)-3-oxa-pentanoic acid-hydrochloride used as the starting material is prepared in the following manner: 1-(2-hydroxyethyl)imidazole (J. Chem. Soc. 1977, 1272) is reacted in the presence of sodium hydride with ethyl chloroacetate in dimethyl formamide to form 5-(imidazol-1-yl)-3-oxa-pentanoic acid-ethyl ester (oil) and the desired acid is obtained from it by heating with 6 N hydrochloric acid.

EXAMPLE 2

R-1-hydroxy-5-(imidazol=1-yl)-3-oxa-hexane-1,1-diphosphonic acid

As described in Example 1, the desired compound is obtained from the R-5-(imidazol-1-yl)-3-oxa-hexanoic acid-hydrochloride (wax-like substance, $[\alpha]°_D$: −12.4°, c =1.4 in water) in a yield of 27% by reaction with phosphorous acid/phosphorus trichloride and subsequent hydrolysis. The substance contains 1 mole water; $[\alpha]°_D$: −10.2°, c=1 in water; $M_{rel}$: 0.30

The R-5-(imidazol-1-yl)-3-oxa-hexanoic acid-hydrochloride used as the starting material is prepared in the following manner: R-2-(imidazol-1-yl)propionic acidethyl ester (Lieb. Ann. 1986, 327) is reduced with lithium aluminium hydride to R-2-(imidazol-1-yl)propanol (oily substance; $[\alpha]°_D$: −17.0°, c=1 in methylene chloride), it is reacted in the presence of sodium hydride with ethyl chloroacetate in dimethyl formamide to form R-5-(imidazol-1-yl)-3-oxa-hexanoic acid-ethyl ester (oily substance, $[\alpha]°_D$: −14.8°, c=1 in methylene chloride) and the desired acid is obtained from it by heating with 6N hydrochloric acid.

EXAMPLE 3

In an analogous manner to that described in Example 1, reaction of phosphorus trichloride/phosphorous acid (which is followed by hydrolysis) with 1.) 6-(imidazol-1-yl)-3-oxa-hexanoic acid-hydrochloride yields 1-hydroxy-6-(imidazol-1-yl)-3-oxa-hexane-1,1-diphosphonic acid
2.) 5-(imidazol-1-yl)-4-methyl-3-oxa-pentanoic acid-hydrochloride yields 1-hydroxy-5-(imidazol-1-yl)-4-methyl-3-oxa-oentane-1,1-diphosohonic acid
3.) S-5-(imidazol-1-yl)-3-oxa-hexanoic acid-hydrochloride yields S-1-hydroxy-5-(imidazol-1-yl)-3-oxa-hexane-1,1-diphosphonic acid
4.) R,S-5-(imidazol-1-yl)-3-oxa-hexanoic acid-hydrochloride yields R,S-1-hydroxy-5-(imidazol-1-yl)-3-oxa-hexane-1,1-diphosphonic acid
5.) 6-(2,4-dimethylimidazol-1-yl)-3-oxa-hexanoic acid-hydrochloride yields 6-(2,4-dimethylimidazol-1-yl)-1-hydroxy-3-oxa-hexane-1,1-diphosphonic acid
6.) 6-(2,5-dimethylimidazol-1-yl)-3-oxa-hexanoic acid-hydrochloride yields 6-(2,5-dimethylimidazol-1-yl)-1-hydroxy-3-oxa-hexane-1,1-diphosphonic acid
7.) 4-(imidazol-1-yl)-3-oxa-pentanoic acid-hydrochloride yields 1-hydroxy-4-(imidazol-1-yl)-3-oxa-oentane-1,1-disphosphonic acid
8.) 5-(2-methylimidazol-1-yl)-4-methyl-3-oxa-pentanoic acid-hydrochloride yields 1-hydroxy-5-(2-methylimidazol-1-yl)-4-methyl-3-oxa-pentane-1,1-diphosphonic acid
9.) R,S-5-(2-methylimidazol-1-yl)-3-oxa-hexanoic acid hydrochloride yields R,S-1-hydroxy-5-(2-methylimidazol-1-yl)-3-oxa-hexane-1,1-diphosphonic acid
10.) S-5-(2-methylimidazol-1-yl)-3-oxa-hexanoic acid hydrochloride yields S-1-hydroxy-5-(2-methylimidazol-1-yl)-3-oxa-hexane-1,1-diphosohonic acid
11.) R-5-(2-methylimidazol-1-yl)-3-oxa-hexanoic acid hydrochloride yields R-1-hydroxy-5-(2-methylimidazol-1-yl)-3-oxa-hexane-1,1-diphosohonic acid
12.) 5-(2-methylimidazol-1-yl)-3-oxa-pentanoic acid hydrochloride yields 1-hydroxy-5-(2-methylimidazol-1-yl)-3-oxa-pentane-1,1-diphosohonic acid
13.) (2-aminoimidazol-1-yl)-3-oxa-pentanoic acid-hydrochloride yields 5-(2-aminoimidazol-1-yl)-1-hydroxy-3-oxa-pentane-1,1-diphosphonic acid
14.) 4-(imidazol-1-yl)-3-oxa-butyric acid-hydrochloride yields 1-hydroxy-4-(imidazol-1-yl)-3-oxa-butane-1,1-diphosphonic acid
15.) 7-(imidazol-1-yl)-3-oxa-heptanoic acid-hydrochloride yields 1-hydroxy-7-(imidazol-1-yl)-3-oxa-heptane-1,1-diphosphonic acid
16.) 7-(2-methylimidazol-1-yl)-3-oxa-heptanoic acid-hydrochloride yields 1-hydroxy-7-(2- methylimidazol-1-yl)-3-oxa-heptane-1,1-diphosphonic acid
17.) 5-(4,5-dihydroimidazol-1-yl)-3-oxa-pentanoic acid-hydrochloride yields 5-(4,5-dihydroimidazol-1-yl)-1-hydroxy-3-oxa-pentane-1,1-diphosphonic acid
18.) 5-(4,5-dihydro-2-methylimidazol-1-yl)-3-oxa-hexanoic acid-hydrochloride yields 5-(4,5-dihydro-2-methylimidazol-1-yl)-1-hydroxy-3-oxa-hexane-1, 1-diphosphonic acid
19.) 5-(4,5-dihydroimidazol-1-yl)-3-oxa-hexanoic acid-hydrochloride yields 5-(4,5-dihydroimidazol-1-yl)-1-hydroxy-3-oxa-hexane-1,1-diphosphonic acid
20.) 5-(4,5-dihydro-2-methylimidazol-1-yl)-4-methyl-3-oxa-pentanoic acid-hydrochloride yields 5-(4,5-dihydro-2-methylimidazol-1-yl)-1-hydroxy-4-methyl-3-oxa-pentane-1,1-diphosphonic acid
21.) 4-(imidazol-2-yl)-3-oxa-butyric acid-hydrochloride yields 1-hydroxy-4-(imidazol-2-yl)-3-oxa-butane-1,1-diphosphonic acid
22.) 4-(1-methylimidazol-2-yl)-3-oxa-butyric acid-hydrochloride yields 1-hydroxy-4-(1-methyl-imidazol-2-yl)-3-oxa-butane-1,1diphosphonic acid
23 ) 4-(1-methylimidazol-2-yl)-3-oxa-pentanoic acid-hydrochloride yields 1-hydroxy-4-(1-methylimidazol-2-yl)-3-oxa-pentane-1,1-diphosphonic acid
24.) 4-(4-bromo-1-methylimidazol-2-yl)-3-oxa-pentanoic acid-hydrochloride yields 4-(4-bromo-1-methylimidazol-2-yl)-1-hydroxy-3-oxa-pentane-1,1-diphosphonic acid
25.) 4-(5-chloro-3-methylimidazol-2-yl)-3-oxa-pentanoic acid-hydrochloride yields 4-(5-chloro-3-methylimidazol-2-yl)-1-hydroxy-3-oxa-pentane-1,1-diphosphonic acid
26.) 5-(imidazol-2-yl)-4-methyl-3-oxa-pentanoic acid-hydrochloride yields 1-hydroxy-5-(imidazol-2-yl)-4-methyl-3-oxa-pentane-1,1-diphosphonic acid
27.) R,S-5-(imidazol-2-yl)-3-oxa-hexanoic acid-hydrochloride yields R,S-1-hydroxy-5-(imidazol-2-yl)-3-oxa-hexane 1,1-diphosphonic acid
28.) S-5-(imidazol-2-yl)-3-oxa-hexanoic acid-hydrochloride yields S-1-hydroxy-5-(imidazol-2-yl)-3-oxa-hexane-1,1-diphosphonic acid
29.) R-5-(imidazol-2-yl)-3-oxa-hexanoic acid-hydrochloride yields R-1-hydroxy-5-(imidazol-2-yl)-3-oxa-hexane-1,1-diphosphonic acid
30.) 5-(imidazol-2-yl)-3-oxa-pentanoic acid-hydrochloride yields 1-hydroxy-5-(imidazol-2-yl)-3-oxa-pentane-1,1-diphosphonic acid
31. 5-(1-methylimidazol-2-yl)-3-oxa-pentanoic acid-hydrochloride yields 1-hydroxy-5-(1-methylimidazol-2-yl)-3-oxa-pentane-1,1-diphosphonic acid
32.) 5-(imidazol-2-yl)-5-methyl-3-oxa-hexanoic acid-hydrochloride yields 1-hydroxy-5-(imidazol-2-yl)5-methyl-3-oxa-hexane-1,1-diphosphonic acid
33.) 4-(imidazol-4-yl)-3-oxa-butyric acid-hydrochloride yields 1-hydroxy-4-(imidazol-4-yl)-3-oxa-butane-1,1-diphosphonic acid
34.) 4-(5-methylimidazol-4-yl)-3-oxa-butyric acid-hydrochloride yields 1-hydroxy-4-(5-methylimidazol-4-yl -3-oxa-butane-1,1-diphosohonic acid
35.) 4-(5-trifluoromethylimidazol-4-yl)-3-oxa-butyric acid-hydrochloride yields 1-hydroxy-4-(5-trifluoromethylimidazol-4-yl)-3-oxa-butane-1,1-diphosphonic acid
36.) 4-(2-methylimidazol-4-yl)-3-oxa-butyric acid-hydrochloride yields 1-hydroxy-4-(2-methylimidazol-4-yl)-3-oxa-butane-1,1-diphosphonic acid
37.) 4-(2-aminoimidazol-4-yl)-3-oxa-butyric acid-hydrochloride yields 4-(2-aminoimidazol-4-yl)-1-hydroxy-3-oxa-butane-1,1-diphosphonic acid
38.) 4-(5-fluoroimidazol-4-yl)-3-oxa-butyric acid-hydrochloride yields 4-(5-fluoroimidazol-4-yl)-1-hydroxy-3-oxa-butane-1,1-diphosphonic acid
39.) 4-(imidazol-4-yl)-3-oxa-pentanoic acid-hydrochloride yields 1-hydroxy-4-(imidazol-4-yl)-3-oxa-pentane-1,1-diphosohonic acid
40.) 4-(1-methylimidazol-4-yl)-3-oxa-pentanoic acid-hydrochloride yields 1-hydroxy-4-(1-methylimidazol-4-yl)-3-oxa-pentane-1,1-diphosphonic acid
41.) 5-(imidazol-4-yl)-3-oxa-pentanoic acid-hydrochloride yields 1-hydroxy-5-(imidazol-4-yl)-3-oxa-pentane-1,1-diphosphonic acid
42.) 5-(2-methylimidazol-4-yl)-3-oxa-pentanoic acid-hydrochloride yields 1-hydroxy-5-(2-methylimidazol-4-yl)-3-oxa-pentane-1,1-diphosphonic acid
43.) 6-(imidazol-4-yl)-3-oxa-hexanoic aoid-hydrochloride yields 1-hydroxy-6-(imidazol-4-yl)-3-oxa-hexane-1,1-diphosphonic acid
44.) 6-(2-methylimidazol-4-yl)-3-oxa-hexanoic acid-hydrochloride yields 1-hydroxy-6-(2-methylimidazol-4-yl)-3-oxa-hexane-1,1-diphosphonic acid
45.) 5-(4-methylimidazol-5-yl)-3-oxa-pentanoic acid-hydrochloride yields 1-hydroxy-5-(4-methylimidazol-5-yl)-3-oxa-pentane-1,1-diphosphonic acid
46.) 5-(imidazol-1-yl)-2-methyl-3-oxa-pentanoic acid-hydrochloride yields 1-hydroxy-5-(imidazol-1-yl)-2-methyl-3-oxa-oentane-1,1-diphosphonic acid
47.) 5-(imidazol-1-yl)-2-methyl-3-oxa-hexanoic acid-hydrochloride yields 1-hydroxy-5-(imidazol-1-yl)-2-methyl-3-oxa-hexane-1,1-diphosphonic acid

EXAMPLE 4

As set forth in Example 1 reaction of ethyl bromoacetate or ethyl chloroacetate, or alpha-bromo- or alpha-chloropropionic acid-ethyl ester (followed by saponification with 2N hydrochloric acid) with 1.) 1-(3-hydroxypropyl)imidazole (prepared by reduction of 3-(imidazol-1-yl)propionic acid-ethyl ester (Bull.Soc.Chim. France 1969, 2835) with lithium aluminium hydride) yields 6-(imidazol-1-yl)-3-oxa-hexanoic acid-hydrochloride
2.) 1-(2-hydroxypropyl)imidazole (J.Chem.Soc. PT 1, 1976, 545) yields 5-(imidazol-1-yl)-4-methyl-3-oxa-pentanoic acid-hydrochloride
3.) S-1-(1-hydroxyprop-2-yl)imidazole (see literature in Example 2) yields S-5-(imidazol-1-yl)-3-oxa-hexanoic acid-hydrochloride
4.) R,S-1-(1-hydroxyprop-2-yl)imidazole (see literature in Example 2) yields R,S-5-(imidazol-1-yl)-3-oxa-hexanoic acid-hydrochloride
5.) 1-(3-hydroxypropyl)-2,4-dimethylimidazole (C.A. 71: 101773 a) yields 6-(2,4-dimethylimidazol-1-yl)-3-oxa-hexanoic acid-hydrochloride
6.) 1-(3-hydroxypropyl)-2,5-dimethylimidazole (C.A. 71: 101773 a) yields 6-(2,5-dimethylimidazol-1-yl)-3-oxa-hexanoic acid-hydrochloride 7.) 1-(1-hydroxyethyl)imidazole (J.Org.Chem. 1967, 2291) yields 4-(imidazol-1-yl)-3-oxa-pentanoic acid-hydrochloride 8.) 1-(2-hydroxypropyl)-2-methylimidazole yields 5-(2-methylimidazol-1-yl)-4-methyl-3-oxa-pentanoic acid-hydrochloride 9.) R,S-1-(1-hydroxyprop-2-yl)-2-methylimidazole yields R,S-5-(2-methylimidazol-1-yl)-3-oxa-hexanoic acid-hydrochloride 10.) S-1-(1-hydroxyprop-2-yl)-2-methylimidazole yields S-5-(2-methylimidazol-1-yl)-3-oxa-hexanoic acid-hydrochloride 11.) R-1-(1-hydroxyprop-2-yl)-2-methylimidazole yields R-5-(2-methylimidazol-1-yl)-3-oxa-hexanoic aoid-hydrochloride 12.) 1-(2-hydroxyethyl)-2-methylimidazole yields 5-(2-methylimidazol-1-yl)-3-oxa-pentanoic acid-hydrochloride 13.) 2-amino-1-(2-hydroxyethyl)imidazole (C.A. 76: 46832 y) yields (2-aminoimidazol-1-yl)-3-oxa-pentanoic acid-hydrochloride 14.) 1-hydroxymethylimidazole yields 4-(imidazol-1-yl)-3-oxa-butyric acid-hydrochloride 15.) 1-(4-hydroxybutyl)imidazole (Brit.Pat. No. 2,016,452) yields 7-(imidazol-1-yl)-3-oxa-heptanoic acid-hydrochloride 16.) 1-(4-hydroxybutyl)-2-methylimidazole (C.A. 99: P 23617 q) yields 7-(2-methylimidazol-1-yl)-3-oxa-heptanoic acid-hydrochloride 17.) 4,5-dihydro-1-(2-hydroxyethyl)imidazole (C.A. 88: 163432 y) yields 5-(4,5-dihydroimidazol-1-yl)-3-oxa-pentanoic acid-hydrochloride 18.) 4,5-dihydro-1-(1-hydroxyprop-2-yl)-2-methylimidazole yields 5-(4,5-dihydro-2-methylimidazol-1-yl)-3-oxa-hexanoic acid-hydrochloride 19.) 4,5-dihydro-1-(1-hydroxyprop-2-yl)imidazole yields 5-(4,5-dihydroimidazol-1-yl)-3-oxa-hexanoic acid-hydrochloride 20.) 4,5-dihydro-1-(2-hydroxypropyl)-2-methylimidazole yields 5-(4.5-dihydro-2-methylimidazol-1-yl)-4-methyl-3-oxa-pentanoic acid-hydrochloride 21.) 2-hydroxymethylimidazole (J.Am.Chem.Soc. 1949, 383) yields 4-(imidazol-2-yl)-3-oxa-butyric acid-hydrochloride 22.) 2-hydroxymethyl-1-methylimidazole yields 4-(1-methylimidazol-2-yl)-3-oxa-butyric acid-hydrochloride 23.) 2-(1-hydroxyethyl)-1-methylimidazole yields 4-(1-methylimidazol-2-yl)-3-oxa-pentanoic acid-hydrochloride 24.) 4-bromo-2-(1-hydroxyethyl)-1-methylimidazole (J.Org.Chem. 1973, 3762) yields 4-(4-bromo-1-methylimidazol-2-yl)-3-oxa-pentanoic acid-hydrochloride 25.) 5-chloro-2-(1-hydroxyethyl)-1-methylimidazole (J.Org.Chem. 1973, 3762) yields 4-(5-chloro-1-methylimidazol-2-yl)-3-oxa-pentanoic acid-hydrochloride 26.) 2-(2-hydroxypropyl)imidazole yields 5-(imidazol-2-yl)-4-methyl-3-oxa-pentanoic acid-hydrochloride 27.) R,S-2-(1-hydroxyprop-2-yl)imidazole yields R,S-5-(imidazol-2-yl)-3-oxa-hexanoic acid-hydrochloride 28.) S-2-(1-hydroxyprop-2-yl)imidazole yields S-5-(imidazol-2-yl)-3-oxa-hexanoic acid-hydrochloride 29.) R-2-(1-hydroxyprop-2-yl)imidazole yields R-5-(imidazol-2-yl)-3-oxa-hexanoic acid-hydrochloride 30.) 2-(2-hydroxyethyl)imidazole yields 5-(imidazol-2-yl)-3-oxa-pentanoic acid-hydrochloride 31.) 2-(2-hydroxyethyl)-1-methylimidazole yields 5-(1-methylimidazol-2-yl)-3-oxa-pentanoic acid-hydrochloride 32.) 2-(;-hydroxy-2-methylprop-2-yl)imidazole (J.Chem.Soc. PT2, 1982, 1511) yields 5-(imidazol-2-yl)-5-methyl-3-oxa-hexanoic acid-hydrochloride 33.) 4-hydroxymethylimidazole (Org.Synthesis 24, 64) yields 4-(imidazol-4-yl)-3-oxa-butyric acid-hydrochloride 34.) 4-hydroxymethyl-5-methylimidazole (J.Med.-Chem. 1976, 923) yields 4-(5-methylimidazol-4-yl)-3-oxa-butyric acid-hydrochloride 35.) 4-hydroxymethyl-5-trifluoromethylimidazole yields 4-(5-trifluoromethylimidazol-4-yl)-3-oxa-butyric acid-hydrochloride 36.) 4-hydroxymethyl-2-methylimidazole (J.Med.-Chem. 1976, 923) yields 4-(2-methylimidazol-4-yl)-3-oxa-butyric acid-hydrochloride 37.) 2-amino-4-hydroxymethylimidazole yields 4-(2-aminoimidazol-4-yl)-3-oxa-butyric acid-hydrochloride 38.) 5-fluoro-4-hydroxymethylimidazole (J.Am.Chem.-Soc. 1973, 4619) yields 4-(5-fluoroimidazol-4-yl)-3-oxa-butyric acid-hydrochloride 39.) 4-(1-hydroxyethyl)imidazole (J.Med.Chem. 1977, 721) yields 4-(imidazol-4-yl)-3-oxa-pentanoic acid-hydrochloride 40.) 4-(1-hydroxyethyl)-1-methylimidazole yields 4-(1-methylimidazol-4-yl)-3-oxa-pentanoic acid-hydrochloride 41.) 4-(2-hydroxyethyl)imidazole (Arch.Pharm. 1974, 517) yields 5-(imidazol-4-yl)-3-oxa-pentanoic acid-hydrochloride 42.) 4-(2-hydroxyethyl)-2-methylimidazole yields 5-(2-methylimidazol-4-yl)-3-oxa-pentanoic acid-hydrochloride 43.) 4-(3-hydroxypropyl)imidazole (J.Het.Chem. 1975, 577) yields 6-(imidazol-4-yl)-3-oxa-hexanoic acid-hydrochloride 44.) 4-(3-hydroxypropyl)-2-methylimidazole yields 6-(2-methylimidazol-4-yl)-3-oxa-hexanoic acid-hydrochloride 45.) 5-(2-hydroxyethyl)-4-methylimidazole yields 5-(4-methylimidazol-5-yl)-3-oxa-pentanoic acid-hydrochloride 46.) 1-(2-hydroxyethyl)imidazole (see Example 1) yields 5-(imidazol-1-yl)-2-methyl-3-oxa-pentanoic acid-hydrochloride 47.) 1-(1-hydroxyprop-2-yl)imidazole (see Example 2) yields 5-(imidazol-1-yl)-2-methyl-3-oxa-hexanoic acid-hydrochloride

EXAMPLE 5

In an analogous manner to that described in Example 1:

1.) 1-hydroxy-6-(imidazol-1-yl)-3-oxa-hexane-1,1-disphosphonic acid is obtained as the free acid with 1 mole water in a yield of 28%; m.p.: 145°–145° C. with decomposition, $M_{rel}$ 0.30, by reacting phosphorus trichloride/-phosphorous acid (after subsequent hydrolysis) with 6-(imidazol-1-yl)-3-oxa-hexanoic acid-hydrochloride (oily substance).

The 6-(imidazol-1-yl)-3-oxa-hexanoic acid-hydrochloride used as the starting material is prepared in the following manner: 1-trimethylsilylimidazole (b.p.$_{20}$: 117°–120° C.) is reacted with chloropropionic acidtrimethylsilyl ester (b.p.$_{1013}$: 172°–175° C.) with simultaneous saponification of the esters to form 3-(imidazol-1-yl)-propionic acid (m.p.: 148°–150° C.). Reaction with trimethylchlorosilane in ethanol leads to the corresponding ethyl ester-hydrochloride from which the free 3-(imidazol-1-yl)-propionic acid-ethyl ester (oil) was obtained with 2N sodium hydroxide solution. The 1-(imidazol-1-yl)-3-propanol (oil) obtained after reduction with lithium aluminium hydride is allowed to react with ethyl bromoacetate in dimethyl formamide in the presence of sodium hydride to form 6-(imidazol-1-yl)-3-oxa-hexanoic acid ethyl ester (oil) which is subsequently saponified with 3N hydrochloric acid to form the desired acid.

2.) 1-hydroxy-5-(imidazol-1-yl)-4-methyl-3-oxa-pentane-1,1-diphosphonic acid is obtained as the free acid with 1 mole water in a yield of 37%; m.p.: 135°–140° C. with decomposition, M$_{ref}$: 0.30, by reacting phosphorus trichloride/phosphorous acid (after subsequent hydrolysis) with 5-(imidazol-1-yl)-4-methyl-3-oxa-pentanoic acid-hydrochloride (oily substance).

The 5-(imidazol-1-yl)-4-methyl-3-oxa-pentanoic acid-hydrochloride used as the starting material was prepared in the following manner: reaction of the sodium salt of the imidazole with propene oxide yields the 2-(imidazol-1-yl)-1-propanol (b.p.$_{0.1}$: 147°–150° C.) from which the 5-(imidazol-1-yl)-4-methyl-3-oxa-pentanoic acid-ethyl ester (oil) is obtained by reaction with ethyl bromoacetate in dimethyl formamide in the presence of sodium hydride which is then saponified with 3N hydrochloric acid to form the desired acid.

What is claimed is:

1. Diphosphonates having the general formula I

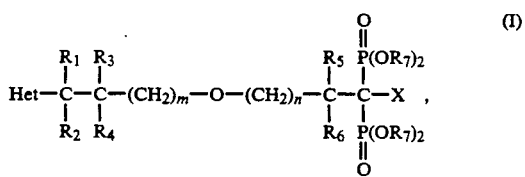

in which
Het is selected from the group consisting of a pyrazolyl, imidazolyl, thiazolyl, isothiazolyl, oxazolyl, isoxazolyl, triazolyl, thiadiazolyl, oxadiazolyl, dithiazolyl and tetrazolyl ring as well as their dihydro and tetrahydro derivatives which ring can be partially hydrogenated and is unsubstituted or substituted at least once by $C_1$–$C_6$ alkyl, halogen, amino or $CF_3$,
$R_1$–$R_7$ are each independently hydrogen or $C_1$–$C_5$ alkyl,
X is hydrogen, OH or —$NR_8R_9$, in which $R_8$ and $R_9$ are, independently hydrogen or $C_1$–$C_5$ alkyl,
m and n are independently 0, 1 or 2, and
their pharmacologically safe salts and optically active forms.

2. Compounds of the formula I as claimed in claim 1, wherein Het denotes imidazolyl or dihydroimidazolyl.

3. Pharmaceutical composition for the treatment of disturbance in calcium metabolism comprising administering an effective amount to treat the disturbance of a diphosphonate of claim 1 and a pharmaceutically acceptable carrier.

4. A method of treating a disturbance in calcium metabolism in a patient in need of such treatment, said method comprising administering to said patient an effective amount of a disphosphonate of claim 1.

5. Method of claim 4, wherein said disturbance is osteoporosis.

6. Compound of claim 1, wherein said compound is selected from the group consisting of
1-hydroxy-5-(imidazol-1-yl)-3-oxa-pentane-1,1-diphosphonic acid
R-1-hydroxy-5-(imidazol-1-yl)-3-oxa-hexane-1,1-diphosphonic acid
1-hydroxy-6-(imidazol-1-yl)-3-oxa-hexane-1,1-diphosphonic acid
1-hydroxy-5-(imidazol-1-yl)-4-methyl-3-oxa-pentane-1,1-diphosphonic acid
S-1-hydroxy-5-(imidazol-1-yl)-3-oxa-hexane-1,1-diphosphonic acid
R,S-1-hydroxy-5-(imidazol-1-yl)-3-oxa-hexane-1,1-diphosphonic acid
6-(2,4-dimethylimidazol-1-yl)-1-hydroxy-3-oxa-hexane-1,1-diphosphonic acid
6-(2,5-dimethyl-imidazol-1-yl)-1-hydroxy-3-oxa-hexane-1,1-diphosphonic acid
1-hydroxy-4-(imidazol-1-yl)-3-oxa-pentane-1,1-disphosphonic acid
1-hydroxy-5-(2-methyl-imidazol-1-yl)-4-methyl-3-oxa-pentane-1,1-diphosphonic acid
R,S-1-hydroxy-5-(2methyl-imidazol-1-yl)-3-oxa-hexane-1,1-diphosphonic acid
S-1-hydroxy-5-(2-methyl-imidazol-1-yl)-3-oxa-hexane-1,1-diphosphonic acid
R-1-hydroxy-5-(2-metyl-imidazol-1-yl)-3-oxa-hexane-1,1-diphosphonic acid
1-hydroxy-5-(2-methylimidazol-1-yl)-3-oxa-pentane-1,1-diphosphonic acid
5-(2-aminoimidazol-1-yl)-1-hydroxy-3-oxa-pentane-1,1-diphosphonic acid
1-hydroxy-4-(imidazol-1-yl)-3-oxa-butane-1,1-diphosphonic acid
1-hydroxy-7-(imidazol-1-yl)-3-oxa-heptane-1,1-diphosphonic acid
1-hydroxy-7-(2-methylimidazol-1-yl)-3-oxa-heptane-1,1-diphosphonic acid
5-(4,5-dihydroimidazol-1-yl)-1-hydroxy-3-oxa-pentane-1,1-diphosphonic acid
5-(4,5-dihydro-2-methylimidazol-1-yl)-1-hydroxy-3-oxa-hexane-1,1-diphosphonic acid
5-(4,5-dihydroimidazol-1-yl)-1-hydroxy-3-oxa-hexane-1,1-diphosphonic acid
5-(4,5-dihydro-2-methylimidazol-1-yl)-1-hydroxy-4-methyl-3-oxa-pentane-1,1-diphosphonic acid
1-hydroxy-4-(imidazol-2-yl)-3-oxa-butane-1,1-diphosphonic acid
1-hydroxy-4-(1-methyl-imidazol-2-yl)-3-oxa-butane-1,1-diphosphonic acid
1-hydroxy-4-(1-methylimidazol-2-yl)-3-oxa-pentane-1,1-diphosphonic acid
4-(4-bromo-1-methylimidazol-2-yl)-1-hydroxy-3-oxa-pentane-1,1-diphosphonic acid
4-(5-chloro-3-methyl-imidazol-2-yl)-1-hydroxy-3-oxa-pentane-1,1-diphosphonic acid
1-hydroxy-5-(imidazol-2yl)-4-methyl-3-oxa-pentane-1,1-diphosphonic acid
R,S-1-hydroxy-5-(imidazol-2-yl)-3-oxa-hexane-1,1-diphosphonic acid
R-1-hydroxy-5-(imidazol-2-yl)-3-oxa-hexane-1,1-diphosphonic acid
R-1-hydroxy-5-(imidazol-2-yl)-3-oxa-hexane-1,1-diphosphonic acid 1-hydroxy-5-(imidazol-2-yl)-3-oxa-pentane-1,1-diphosphonic acid
1-hydroxy-5-(1-methylimidazol-2-yl)-3-oxa-pentane-1,1-diphosphonic acid
1-hydroxy-5-(imidazol-2-yl)-5-methyl-3-oxa-hexane-1,1-diphosphonic acid
1-hydroxy-4-(imidazol-4-yl)-3-oxa-butane-1,1-diphosphonic acid
1-hydroxy-4-(5-methyl-imidazol-4-yl)-3-oxa-butane-1,1-diphosphonic acid
1-hydroxy-4-(5-trifluoromethylimidazol-4-yl)-3-oxa-butane-1,1-diphosphonic acid
1-hydroxy-4-(2-methylimidazol-4-yl)-3-oxa-butaine-1,1-diphosphonic acid
4-(2-aminoimidazol-4-yl)-1-hydroxy-3-oxa-butane-1,1-diphosphonic acid
4-(5-fluoroimidazol-4-yl)-1-hydroxy-3-oxa-butane-1,1-diphosphonic acid
1-hydroxy-4-(imidazol-4-yl)-3-oxa-pentane-1,1-diphosphonic acid
1-hydroxy-4-(1-methylimidazol-4-yl)-3-oxa-pentane-1,1-disphosphonic acid
1-hydroxy-5-(imidazol-4-yl)-3-oxa-pentane-1,1-disphosphonic acid
1-hydroxy-5-(imidazol-4-yl)-3-oxa-pentane-1,1-diphosphonic acid
1-hydroxy-5-(2-methylimidazol-4-yl)-3-oxa-pentane-1,1-diphosphonic acid
1-hydroxy-6-(imidazol-4-yl)-3-oxa-hexane-1,1-diphosphonic acid
1-hydroxy-6-(2-methylimidazol-4-yl)-3-oxa-hexane-1,1-diphosphonic acid
1-hydroxy-5-(4-methylimidazol-5-yl)-3-oxa-pentane-1,1-diphosphonic acid
1-hydroxy-5-imidazol-1-yl)-2-methyl-3-oxa-pentane-1,1-diphosphonic acid
1-hydroxy-5-(imidazol-1-yl)-2-methyl-3-oxa-hexane-1,1-diphosphonic acid
6-(imidazol-1-yl)-3-oxa-hexanoic acid
5-(imidazol-1-yl)-4-methyl-3-oxa-pentanoic acid
S-5-(imidazol-1-yl)-3-oxa-hexanoic acid
R,S-5-(imidazol-1-yl)-3-oxa-hexanoic acid
6-(2,4-dimethylimidazol-1-yl)-3-oxa-hexanoic acid-hydrochloride
6-(2,5-dimethylimidazol-1-yl)-3-oxa-hexanoic acid-hydrochloride
4-(imidazol-1-yl)-3-oxa-pentanoic acid
5-2(2-ethylimidazol-1-yl)-4-methyl-3-oxa-pentanic acid-hydrochloride
R,S-5-(2-methylimidazol-1-yl)-3-oxa-hexanoic acid
R-5-(2-methylimidazol-1-yl)-3-oxa-hexanoic acid
5-(2methylimidazol-1-yl)-3-oxa-pentanoic acid
(2-aminoimidazol-1-yl)-3-oxa-pentanoic acid
4-(imidazol-1-yl)-3-oxa-butyric acid
7-(imidazol-1-yl)-3-oxa-heptanoic acid
7-(2-methylimidazol-1-yl)-3-oxa-heptanoic acid
5-(4,5-dihydroimidazol-1-yl)-3-oxa-pentanoic acid
5-(4,5-dihydro-2-methylimidazol-1-yl)-3-oxa-hexanoic acid
5-(4,5-dihydroimidazol-1-yl)-3-oxa-hexanoic acid
5-(4,5-dihydro-2-methylimidazol-1-yl)-4-methyl-3-oxa-pentanoic acid
4-(imidazol-2-yl)-3-oxa-butyric acid
4-(1-methylimidazol-2-yl)-3-oxa-butyric acid
4-(1-methylimidazol-2-yl)-3-oxa-pentanoic acid
4-(4-bromo-1-methylimidazol-2-yl)-3-oxa-pentanoic acid
4-(5-chloro-1-methylimidazol-2-yl)-3-oxa-pentanoic acid
5-(imidazol-2-yl)-4-methyl-3-oxa-pentanoic acid
R,S-5-(imidazol-2-yl)-3-oxa-hexanoic acid
S-5-(imidazol-2-yl)-3-oxa-hexanoic acid
R-5-(imidazol-2-yl)-3-oxa-hexanoic acid
5-(imidazol-2-yl)-3-oxa-pentanoic acid
5-(1-methylimidazol-2-yl)-3-oxa-pentanoic acid
5-(imidazol-2-yl)-5-methyl-3-oxa-hexanoic acid
4-(imidazol-4-yl)-3-oxa-butyric acid
4-(5-methylimidazol-4-yl)-3-oxa-butyric acid
4-(5-trifluoromethylimidazol-4-yl)-3-oxa-butyric acid
4-(2-methylimidazol-4-yl)-3-oxa-butyric acid
4-(2-aminoimidazol-4-yl)-3-oxa-butyric acid
4-(5-fluoroimidazol-4-yl)-3-oxa-butyric acid
4-(imidazol-4-yl)-3-oxa-pentanoic acid
4-(1-methylimidazol-4-yl)-3-oxa-pentanoic acid
5-(imidazol-4-yl)-3-oxa-pentanoic acid
6-(imidazol-4-yl)-3-oxa-hexanoic acid
6-(2-methylimidazol--yl)-3-oxa-hexanoic acid
5-(4-methylimidazol-5-yl)-3-oxa-pentanoic acid
5-(imidazol-1-yl)-2-methyl-3-oxa-pentanoic acid
5-(imidazol-1-yl)-2-methyl-3-oxa-hexanoic acid
1-hydroxy-6-(imidazol-1-yl)-3-oxa-hexane-1,1-disphosphonic acid
1-hydroxy-5-(imidazol-1-yl)-4-methyl-3-oxa-pentane-1,1-diphosphonic acid
5-(imidazol-1-yl)-3-oxa-pentane-1,1-diphosphonic acid
5-(imidazol-1-yl)-3-oxa-hexane-1,1-diphosphonic acid
S-5-(imidazol-1-yl)-3-oxa-hexane-1,1-diphosphonic acid
R-5-(imidazol-1-yl)-3-oxa-hexane-1,1-diphosphonic acid
5-(imidazol-1-yl)-4-methyl-3-oxa-pentane-1,1-diphosphonic acid
5-(2-methylimidazol-1-yl)-3-oxa-hexane-1,1-diphosphonic acid
5-(4,5-dihydro-2-methylimidazol-1-yl)-3-oxa-hexane-1,1-diphosphonic acid
4-(imidazol-2-yl)-3-oxa-butane-1,1-diphosphonic acid
5-(imidazol 2-yl)-3-oxa-pentane-1,1-diphosphonic acid
5-(imidazol-2-yl)-3-oxa-hexane-1,1-diphosphonic acid
5-(imidazol-2-yl)-4-methyl-3-oxa-pentane-1,1-diphosphonic acid
4-(imidazol-4-yl)-3-oxa-butane-1,1-diphosphonic acid
5-(imidazol-4-yl)-3-oxa-pentane-1,1-diphosphonic acid
1-amino-5-(imidazol-1-yl)-3-oxa-hexane-1,1-diphosphonic acid
1-dimethylamino-5-(imidazol-1-yl)-3-oxa-hexane-1,1-diphosphonic acid
and pharmaceutically acceptable salts thereof.

* * * * *